United States Patent
Horstmann et al.

(10) Patent No.: US 11,291,745 B2
(45) Date of Patent: Apr. 5, 2022

(54) WATER-VAPOR-PERMEABLE ADHESIVE BANDAGES

(71) Applicant: LTS Lohmann Therapie-Systeme AG, Andernach (DE)

(72) Inventors: Michael Horstmann, Neuwied (DE); Christian Hausen, St. Katharinen (DE); Patrick Mohr, Bad Breisig (DE); Karin Ludwig, Datzeroth (DE); Tobias Kleudgen, Ettringen (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 482 days.

(21) Appl. No.: 16/239,862

(22) Filed: Jan. 4, 2019

(65) Prior Publication Data

US 2019/0134254 A1    May 9, 2019

Related U.S. Application Data

(63) Continuation of application No. 13/383,048, filed as application No. PCT/EP2010/004029 on Jul. 3, 2010, now abandoned.

(30) Foreign Application Priority Data

Jul. 14, 2009 (DE) .................... 10 2009 032 866.1
Nov. 12, 2009 (DE) .................... 10 2009 052 943.8

(51) Int. Cl.
| | | |
|---|---|---|
| *A61L 15/44* | (2006.01) | |
| *A61L 15/24* | (2006.01) | |
| *A61L 15/58* | (2006.01) | |

(52) U.S. Cl.
CPC ............ *A61L 15/44* (2013.01); *A61L 15/24* (2013.01); *A61L 15/58* (2013.01); *A61L 2300/408* (2013.01); *A61L 2300/608* (2013.01)

(58) Field of Classification Search
CPC .......... A61L 15/58; A61L 15/60; A61L 26/00; A61L 15/44; A61L 15/24; A61L 2300/408; A61L 2300/608; A61L 15/16; A61L 2300/404; A61L 2300/40; A61L 2300/62; A61L 24/00; A61L 24/001; A61L 24/0015; A61L 24/0031; A61L 24/0047; A61L 2300/00; A61L 15/585; A61L 15/42; A61L 15/00; C08L 25/04; A61F 5/443; A61F 2013/00089; A61F 2013/00757; A61F 2013/00582; A61F 2013/00246; A61F 13/00; A61F 13/0266; A61F 13/00085; A61F 13/0233; A61F 13/0243; A61F 13/0246; A61F 13/0253; A61F 13/0256; A61F 13/0259; A61F 13/00063; A61F 13/60; A61F 13/069; A61K 9/7053; A61K 9/7076; A61K 9/703; A61K 9/7038; A61K 9/7023
USPC ........ 602/41–43, 52, 54, 59, 48, 56, 57, 58; 604/304, 307; 424/445, 443, 446–448; 128/889–894
See application file for complete search history.

(56) References Cited

U.S. PATENT DOCUMENTS

| | | | |
|---|---|---|---|
| 3,339,546 A | 9/1967 | Chen | |
| 4,231,369 A | 11/1980 | Sorensen et al. | |
| 4,367,732 A | 1/1983 | Poulsen et al. | |
| 5,088,483 A * | 2/1992 | Heinecke | A61F 13/023 128/849 |
| 5,527,536 A * | 6/1996 | Merkle | A61K 9/7053 424/448 |
| 2006/0147509 A1 | 7/2006 | Kirkby et al. | |
| 2007/0259029 A1* | 11/2007 | McEntire | A61K 8/85 424/449 |

FOREIGN PATENT DOCUMENTS

| | | | | |
|---|---|---|---|---|
| DE | 102009032866.1 A1 | 1/2011 | | |
| EP | 0 157 960 A1 | 10/1985 | | |
| JP | 06/016542 A | 1/1994 | | |
| WO | 03/002684 A1 | 1/2003 | | |
| WO | WO-03002684 A1 * | 1/2003 | ........... | B65D 25/205 |
| WO | 2005/051333 A1 | 6/2005 | | |
| WO | WO-2005051333 A1 * | 6/2005 | ............ | A61L 15/60 |
| WO | 2006130461 A1 | 12/2006 | | |

OTHER PUBLICATIONS

Polymer Properties Database: "Rosin Esters and Polymers"; accessed from https://polymerdatabase.com/ (Year: 2015).*

* cited by examiner

*Primary Examiner* — Caitlin A Carreiro
(74) *Attorney, Agent, or Firm* — ProPat, LLC; Vinisha Joshi

(57) ABSTRACT

Adhesive bandages are provided with a water-vapor permeable back layer and an adhesive layer, in which the adhesive layer includes 10 weight percent of a disperse internal phase of hydrophilic particles that are water-swellable in an outer phase that includes at least 10 weight percent of a styrene block copolymer and at least 20 weight percent of an ester resin of colophony, and that can further contain at least one anti-virus substance.

11 Claims, No Drawings

WATER-VAPOR-PERMEABLE ADHESIVE BANDAGES

CROSS-REFERENCE TO RELATED APPLICATION

This continuation application claims priority to U.S. patent application Ser. No. 13/383,048, filed Jan. 9, 2012, pending, which claims priority to PCT/EP2010/004029, filed Jul. 3, 2010, which further claims priority to its parent applications, German Patent Application No. 10 2009 032 866.1, filed Jul. 14, 2009 and German Patent Application No. 10 2009 052 943.8, filed Nov. 12, 2009, U.S. patent application Ser. No. 13/383,048, International Application No. PCT/EP2010/004029, German Patent Application No. 10 2009 032 866.1 and German Patent Application No. 10 2009 052 943.8 are each hereby incorporated by reference herein in their entirety.

FIELD OF THE INVENTION

The present invention relates to skin plasters, i.e. plasters for covering an area of the surface of a living being, which can adhere to the skin, as in patent application DE 10 2009 032 866.1. The invention relates in particular to skin plasters with a high water-vapor permeability.

BACKGROUND OF THE INVENTION

Usually, plasters for treating or preventing wounds or pressure points comprise a back layer and an adhesive layer. The back layer can be occlusive, i.e. impermeable to water vapor, and, as a result, cause an increase in undesired moisture underneath (= in the area of the application site of) the skin plaster, which leads to skin irritations and shortened wearing time.

There have been numerous attempts to develop skin plasters with an increased water-vapor permeability which allow an evaporation of moisture that arises on the surface of the skin through the skin plaster. As a result, an undesired accumulation of moisture and the associated detachment of the skin plaster or increase in the level of bacteria underneath the skin plaster can be avoided.

The problem for the person skilled in the art when developing water-vapor-permeable skin plasters consists in providing a skin-compatible pressure-sensitive adhesive which at the same time has a high adhesive power and a high water-vapor permeability and/or water-absorption capacity.

The prior art discloses, for example, water-containing adhesives which are based virtually entirely on water-soluble polymers. However, the adhesive power of the water-containing adhesives is perceived as inadequate. Moreover, skin plasters with an adhesive layer based on water-soluble polymers come off after a wearing time of a few hours because the adhesive layer dries out and, in so doing, loses its adhesive power.

The prior art also describes hydrocolloid adhesive masses for producing non-occlusive skin plasters. Classic hydrocolloid adhesive masses are traditionally produced from vegetable gums with the addition of further natural products and are as a rule applied in a thick layer. Such masses are used for example as edge adhesive masses for colostomy bags.

Particularly suitable hydrocolloid adhesive masses are described in U.S. Pat. No. 3,339,546, in particular an adhesive mass comprising polyisobutylenes and one or more hydrocolloids which can swell in aqueous liquids.

Further examples of hydrocolloid adhesive masses are known from U.S. Pat. Nos. 4,231,369 and 4,367,632.

U.S. Pat. No. 4,231,369 discloses a sealing material for colostomy bags, comprising at least one crosslinked elastomer as basis for an external, continuous phase in which at least one hydrocolloid is dispersed. The elastomer can be a styrene-olefin-styrene block copolymer or an ethylene-propylene block copolymer. In addition, the outer phase comprises a tackifier from the group of polymers and copolymers of dicyclopentadiene, alpha-pinene or beta-pinene.

U.S. Pat. No. 4,367,732 relates to skin plasters consisting of an elastic film and a weakly elastic adhesive. This adhesive comprises:
(I) a continuous phase comprising
  (a) a physically crosslinked elastomer in the form of a styrene-isoprene-styrene block copolymer or ethylene-propylene block copolymer,
  (b) a hydrocarbon resin in the form of a polymer or copolymer of cyclopentadiene, dicyclopentadiene, alpha-pinene and/or beta-pinene,
  (c) an antioxidant,
  (d) optionally an oil extender consisting of one or more mineral oils, and
  (e) optionally a plasticizer, which is polar to the elastomer, for example an ester of a polyethylene glycol or polypropylene glycol, or an ester of a di- or polybasic carboxylic acid with a preferably aliphatic alcohol, and
(II) a phase dispersed in the continuous phase and comprising one or more water-swellable hydrocolloids.

The elastic film which forms the back layer should be water-impermeable, preference being given to an elastic, water-impermeable polyurethane film.

The adhesive in the case of the skin plaster can be present in the form of a relatively thin layer, which has a thickness of 0.25 to 3 mm and preferably a thickness of about 1.1 mm.

In more recent times, very thin skin plasters with and without the addition of water-swellable particles have also been developed. For example, WO 2006/130461 A1 discloses thin, non-occlusive skin plasters for treating virus-induced lesions. These skin plasters comprise a back layer and an adhesive layer which is essentially free from hydrocolloid particles. The skin plasters reportedly have a thickness of only 10 to 1500 µm, it being described how the adhesive layer can be between 20 and 200 µm in thickness.

WO 2005/051333 A1 describes skin plasters which have a water-vapor-permeable back layer and a skin-friendly, hydrocolloid-particle-containing adhesive layer. The thickness of the adhesive layer of these skin plasters is at least in the edge region of the skin plaster 20 to 300 µm, the water-vapor permeability of the skin plasters is 200 to 1000 g/m$^2$ and the moisture absorption of the skin plaster is 40 to 600 g/m$^2$/6 h.

The plasters known from the prior art, however, do not have a satisfactory adhesive power coupled with adequately high water-vapor permeability.

SUMMARY OF ADVANTAGEOUS EMBODIMENTS OF THE INVENTION

The object of the present invention was therefore to provide skin plasters which have a good adhesive power coupled with high water-vapor permeability.

DETAILED DESCRIPTION OF ADVANTAGEOUS EMBODIMENTS OF THE INVENTION

Surprisingly, the object is achieved by a skin plaster which comprises a back layer made of a water-vaporpermeable material, preferably a film of polyurethane, and an adhesive layer which comprises 10% by weight of a disperse inner phase of hydrophilic, water-swellable particles in an external phase comprising at least 10% by weight of a styrene block copolymer and at least 20% by weight of an ester resin of colophony.

The back layer of the skin plaster according to the invention is water-vapor permeable. Materials that are suitable in principle for a back layer are polyolefin films, for example made of polyethylene or polypropylene, polyvinyl chloride films, polyether amide films, polyamide films, polyester films, ethylene vinyl acetate films, woven fabrics, knitted fabrics, foams and polyurethane films. Within the context of the invention, the term "films" is used both for polymer films and for polymer foils.

The back layer can be monolithic provided it has the required water-vapor permeability. However, the back layer can also be microporous or perforated in order to make an otherwise water-vapor-impermeable polymer film water-vapor-permeable.

Preferably, the back layer is water-impermeable, but water-vapor-permeable.

The preferred material for the back layer is a low-friction, flexible polymer film. Particularly preferred materials for the back layer are water-vapor-permeable polyurethane films. The back layer has a suitable thickness for the intended use. The use of thinner back layers leads to skin plasters with better extensibility and ability to adapt to the surface of the body.

Preferably, the back layer has a thickness of less than 30 µm, particularly preferably of less than 20 µm and very particularly preferably of less than 18 µm. The back layer can even have a thickness of less than 15 µm, for example a thickness of 12 µm.

The water-vapor permeability of the back layer is at least 200 g/24 hours, preferably at least 800 g/24 hours. The water-vapor permeability is up to 1300 g/24 hours, preferably up to 6000 g/24 hours.

The adhesive layer of the skin plaster according to the invention consists of an adhesive which has a continuous outer phase and an inner phase dispersed in this outer phase. The continuous outer phase comprises at least 10% by weight of a styrene block copolymer and at least 20% by weight of an ester resin of colophony. The weight percentage data refers to the mass of the adhesive. The inner phase consists of hydrophilic, water-swellable particles and constitutes at least 10% by weight of the adhesive mass.

The adhesive composition forming the external phase of the adhesive layer of the skin plasters according to the invention comprises a styrene block copolymer. The styrene block copolymer is preferably an elastomer from the group of styrene-olefin-styrene block copolymers. The olefin block can be based on isoprene, butadiene, other short-chain alkadienes or alkanes, such as, for example, mixtures of ethylene and butylene, or polyisobutylene, and also of combinations of these compounds. Styrene block copolymers that are particularly preferred for the outer phase are styrene-isoprene-styrene block copolymers.

The outer phase of the adhesive for the adhesive layer of the skin plasters according to the invention further comprises at least one ester resin of colophony.

Colophony is a natural resin which is obtained from the balsam of conifers. It is the non-distillable, solid residue of conifer balsam. The distillate is referred to as terpentine oil and comprises alpha-pinene and beta-pinene as main constituents. Colophony consists of a mixture of resin acids and terpenes. The main constituent of colophony is easy-to-oxidize resin acids such as abietic acid and pimaric acid. By reacting the resin acids of colophony with polyols such as pentaerythritol, glycerol or glycols, the so-called colophony esters are obtained, which are also referred to as ester resins of colophony.

Consequently, within the context of the present invention, the term "ester resins of colophony" also includes esters of the resin acids, in particular esters of abietic acid and/or of pimaric acid, to which expressly also the esters with pentaerythritol, glycerol or glycols belong.

The preparation of colophony esters usually takes place by batch processes in the molten state at very high temperatures (250 to 300° C.).

Preferably, the ester resins of colophony for the skin plasters according to the invention are esters of glycerol, esters of pentaerythritol or mixtures of these esters.

The adhesive for the adhesive layer of the skin plasters according to the invention comprises hydrophilic, water-swellable particles. Preferably, the hydrophilic, water-swellable particles are hydrocolloid particles.

"Hydrocolloids" are understood as meaning a large group of polysaccharides and proteins which dissolve in water as colloids and display a high ability for gel formation. Virtually all hydrocolloids are of natural origin. They are either naturally occurring hydrophilic polymers or their chemically modified variants. The hydrocolloids include, for example, starch, celluloses such as carboxymethylcellulose, chitosan, pectins, gum arabic, guar seed flour, carob seed flour, agar, carrageenan, alginates, gelatin, caseinates, dextrins and xanthan.

For the hydrophilic, water-swellable particles, synthetic polymers of the same or different monomers are also suitable. Suitable hydrophilic, water-swellable particles can consist, for example, of polyacrylic acid, polyvinyl alcohol, polyvinyl acetate, polyhydroxyalkyl acrylates, polyhydroxyalkyl methacrylates, polyacrylamides, polystyrene sulfonates, polyvinylpyrrolidone, polyglycols, copolymers, graft copolymers and mixtures of said polymers.

The hydrophilic, water-swellable particles have an average size of less than 125 µm, they are preferably smaller than 100 µm, particularly preferably smaller than 75 µm and very particularly preferably smaller than 50 µm.

By virtue of the content of hydrophilic water-swellable particles in the adhesive layer, especially as an inner phase contained within an external adhesive composition, the skin plasters according to the invention achieve good conditions for a moist wound healing.

Although not wishing to be bound by theory, Applicants believe that the inventive elevated water permeability values are obtained due to the composition of the pressure-sensitive adhesive with hydrophilic water-swellable particles suspended within an "outer" phase adhesive. Particularly, the water-swellable particles absorb water molecules from the skin surface and promote transport of such water molecules through the adhesive layer to ultimately evaporate from the skin-distant side of the patch. Applicants have found that the fairly elevated quantity of the hydrophilic material, such as at least 10%, and their presence as "particles" (=particulate matter) further promote the inventive water molecule transport. Applicants have further found that outer phase adhesive based upon styrene block copolymers combined with a tackifier promotes even greater water molecule transport from the water-swellable particles, without loss to adhesive power. In particular, a specific property of styrene block copolymers is the ability of the "styrene blocks" to form "semicrystalline" regions within the resulting polymeric material. These semicrystalline regions are relatively rigid and responsible for a relatively tight linkage of the polymer chains, giving rise to polymer cohesion and adhesion. However, the "non styrene blocks" within styrene block copolymers (e.g. isoprene in the case of styrene isoprene block copolymers or butadiene in the case of styrene butadiene block copolymers) are not particularly rigid, but are instead relatively elastic. Applicants have found that styrene block copolymers—while being hydrophobic—are nevertheless capable of incorporating suspended particles of hydrophilic water-swellable particles, which Applicants hypothesize are located in the "elastic regions" formed by the "non-styrene blocks" of the styrene block copolymer, leaving the semi-crystalline styrene regions intact. Applicants have determined that this intact semi-crystalline region of the styrene block copolymers imparts adhesive and cohesive properties, the elastic region retains the suspended hydrophilic particles, and the hydrophilic water-swellable particles promotes water transport, resulting in an adhesive layer that has both a high adhesive power and a high water-vapor permeability and/or water-absorption capacity. In especially expedient embodiments, the styrene block copolymer is KRATON™ D, a linear block copolymer based on styrene and isoprene, which features high strength, good elasticity and does not require a crosslinking reaction. In especially advantageous aspects of such embodiments, the inventive adhesive contains styrene isoprene copolymer as the styrene block copolymer component (and the only copolymer component) and a glycol ester of dehydrogenated colophony as the colophony component. In such aspects, the glycol ester of dehydrogenated colophony is preferably present at a weight ratio of 2:1 to about 3:1 relative to styrene isoprene block copolymer.

The adhesive layer of the skin plaster according to the invention can be relatively thick, for example up to 1 mm, preferably up to 3 mm and particularly preferably up to 5 mm.

According to preferred embodiments, however, the adhesive layer of the skin plasters according to the invention is a comparatively thin layer which is not thicker than 300 µm, preferably not thicker than 200 µm, particularly preferably not thicker than 150 µm and very particularly preferably not thicker than 100 µm. The lower limit which can be given for the thickness of the adhesive layer is 25 µm, preferably 30 µm. Thin adhesive layers are preferred because the resulting skin plaster is also thin and therefore more flexible.

The thickness of the adhesive layer of the skin plaster according to the invention can be essentially constant over the entire surface of the skin plaster. In preferred embodiments, however, the adhesive layer is thicker in the middle of the skin plaster than at the edge region. An adhesive layer which tapers to the edge of the skin plaster avoids the skin plaster rolling up off the skin and thus prolongs the possible wearing time. In the case of thin adhesive layers, however, it is also possible to dispense with a tapering at the edge region without the possible wearing time being significantly impaired.

The skin plasters according to the invention are water-vapor-permeable. The water-vapor permeability of the skin plasters according to the invention is at least 50 g/m$^2$, preferably at least 80 g/m$^2$, particularly preferably at least 100 g/m$^2$, in a period of 24 hours. The water-vapor permeability of the skin plasters according to the invention is usually below 1000 g/m$^2$, in the case of specific embodiments below 400 g/m$^2$, preferably below 250 g/m$^2$, particularly preferably below 150 g/m$^2$, based on a period of 24 hours.

On account of the hydrophilic, water-swellable particles in the adhesive layer, the skin plasters according to the invention are able to absorb a certain amount of moisture.

The amount of moisture which can be absorbed is dependent, inter alia, on the thickness of the adhesive layer, the material of the hydrophilic, water-swellable particles and their content in the adhesive layer.

In preferred embodiments, the skin plaster according to the invention has an absorption capacity of at least 40 g/m$^2$/6 h, preferably of at least 50 g/m$^2$/6 h, particularly preferably of at least 60 g/m$^2$/6 h and very particularly preferably of at least 70 g/m$^2$/6 h. The absorption capacity is up to 250 g/m$^2$/6 h, preferably up to 300 g/m$^2$/6 h, particularly preferably up to 400 g/m$^2$/6 h and very particularly preferably up to 600 g/m$^2$/6 h. The absorption capacity is determined by immersing a skin plaster completely in physiological sodium chloride solution (0.9 M NaCl in water) at a temperature of 37° C. for a duration of 6 hours, and then determining the absorbed amount of water.

The skin plaster according to the invention can have a covering which absorbs moisture or wound exudate. The absorbent covering is situated on the surface of the adhesive layer which faces the back layer. The absorbent layer can consist of any desired suitable material, for example gauze, alginates, collagens, foams, superabsorbents or the like. Coverings of this kind and the materials suitable for them are known to the person skilled in the art.

The skin plasters according to the invention are suitable for covering cut wounds or graze wounds, and also scars, other skin lesions and the like.

In one particular embodiment, the skin plasters according to the invention comprise an antiviral active ingredient or a mixture of antiviral active ingredients in the adhesive layer.

The antiviral active ingredient, at least one of the antiviral active ingredients or the antiviral active ingredients is/are preferably selected from the group of active ingredients which includes aciclovir, valaciclovir, penciclovir, famciclovir, brivudine, adenine arabinoside and phosphonoformic acid, also known under the proprietary name Foscarnet.

The antiviral active ingredient, at least one of the antiviral active ingredients or the antiviral active ingredients can also be selected from the group of active ingredients which comprises silicic acid, n-docosanol and idoxuridine. Although these active ingredients are not primarily considered to be antiviral, they nevertheless have a good antiviral effectiveness.

The content of antiviral active ingredient or of antiviral active ingredients in the adhesive layer is at least 0.1% by weight, preferably at least 1.0% by weight, based on the mass of the active-ingredient-containing adhesive layer. The active-ingredient-containing adhesive layer can comprise up to 20% by weight of active ingredient, but preferably comprises not more than 10% by weight, in each case based on the mass of the active-ingredient-containing adhesive layer. It is known to the person skilled in the art that the amount of active ingredient to be used depends on the active ingredient to be used or the active ingredient mixture to be used.

The embodiments of the skin plasters according to the invention which comprise at least one antiviral active ingredient are suitable for covering skin lesions which are caused by an infection with viruses, for example the so-called "herpes blisters" in the case of an infection with *Herpes simples labialis*.

The skin plasters according to the invention have a removable protective layer or protective film ("release liner") which covers the adhesive layer on its surface facing the back layer. The adhesive surface can be covered completely by a single-part protective layer, or two or more protective layers can partly cover the adhesive surface, it being preferred for the entire adhesive surface to be covered. The protective layer(s) or protective film(s) is/are to be removed prior to or while applying the skin plaster to the skin.

Suitable material for the protective layer is, for example, siliconized paper or plastic films, for example made of polyethylene terephthalate, polyester, polyethylene, which are optionally provided with a nonstick coating. Materials for a protective layer for covering an adhesive layer of skin plasters are known to the person skilled in the art.

It is not necessary for the protective layer to have the same size and/or shape as the skin plaster. It is, for example, possible to apply two or more skin plasters to a single protective layer or a plurality of common protective layers.

In particular, a single-part protective layer can also be designed as part of the primary packaging for the skin plaster according to the invention.

The skin plasters according to the invention can be produced using known methods for producing skin plasters.

The skin plasters according to the invention are exceptionally suitable for a use as covering of cut wounds or graze wounds, scars, skin lesions and the like, where they have a good water-vapor permeability and at the same time a high adhesive power. The skin plasters according to the invention are thus characterized by a long wearing time and, with them, it is also possible to create optimum conditions for moist wound healing without resulting in an undesired accumulation of moisture underneath the skin plaster.

The invention is illustrated by the following working examples:

EXAMPLE 1

289.56 g of FORAL™ 85E (a glycol ester of dehydrogenated colophony from Eastman) are added, with stirring, to 288.01 g of special-boiling-point spirit 80/110 and homogenized.

99.23 g of KRATON™ D 1161 NU (a linear block copolymer based on styrene and isoprene from Kraton Polymer) are then added. The mixture is homogenized. Finally, 43.2 g of Na carboxymethylcellulose (CRT 60000 SPA 07) are added and the mixture is stirred until completely homogeneous.

The mixture is spread in a thickness of 200 µm on a polyurethane film on support paper (type U 50, 55 g/m² from Smith & Nephew). The layered mass is dried in the drying cabinet for 40 min at room temperature and then for 30 min at 60° C. This results in a weight per unit area of 100 g/m². It is covered with a release liner (brand: Silphan 100 µm tsp AB1, 140 g/m²).

EXAMPLE 2

72.4 g of FORAL™ 85E and, in three portions, 24.8 g of KRATON™ D1161 are added, with stirring, to 72.0 g of special-boiling-point spirit 80/110. 10.8 g of sodium carboxymethylcellulose are then added to the mass and homogenized with stirring. The bubble-free mass is applied in a coating thickness of 200 µm to a siliconized PE film and brought from room temperature to 60° C. in the drying cabinet with increasing temperature (1°/min).

The resulting laminate with a weight per unit area of 98 g/m² is covered with a PU film of thickness 50 µm. Round plasters with an area of 1.77 cm² are punched from the present laminate.

That which is claimed:

1. A skin plaster comprising a water-vapor-permeable back layer and an adhesive layer;
    the adhesive layer consisting of an inner phase dispersed within an outer phase and at least one antiviral active ingredient, wherein the adhesive layer has a thickness of between 25 µm to 300 µm;
    the at least one antiviral active ingredient being selected from a group consisting of aciclovir, valacyclovir, penciclovir, famciclovir, brivudine, adenine arabinoside, n-docosanol and idoxuridine;
    the inner phase consisting of hydrophilic, water-swellable particles having an average size of less than 125 µm and which constitute at least 10% by weight of said adhesive layer;
    the outer phase consisting of an adhesive composition that consists of a glycol ester of dehydrogenated colophony and a styrene isoprene block copolymer as the only copolymer in the adhesive composition, wherein said styrene isoprene block copolymer constitutes at least 10% by weight of said adhesive layer and said glycol ester of dehydrogenated colophony constitutes at least 20% by weight of said adhesive layer, and wherein said glycol ester of dehydrogenated colophony is present at a weight ratio of 2:1 to about 3:1 relative to said styrene isoprene block copolymer; and
    wherein the skin plaster exhibits a water vapor permeability in a period of 24 hours of at least 50 g/m² and less than 1000 g/m², and has an absorption capacity of at least 40 g/m²/6 hours up to 600 g/m²/6 hours.

2. The skin plaster as claimed in claim 1, wherein the hydrophilic, water-swellable particles are hydrocolloids.

3. The skin plaster as claimed in claim 1, wherein the hydrophilic, water-swellable particles comprise compounds selected from the group consisting of starch flour, celluloses, chitosan, pectin, gum arabic, guar seed flour, carob seed flour, agar, carrageenan, alginates, gelatin, caseinates, dextrins, xanthan, or synthetic polymers selected from polyacrylic acids, polyvinyl alcohols, polyvinyl acetates, polyhydroxyalkyl acrylates, polyhydroxyalkyl methacrylates, polyacrylamides, polystyrenesulfonates, polyvinylpyrrolidones, polyglycols, copolymers, graft copolymers and mixtures of said polymers.

4. The skin plaster as claimed in claim 1, wherein the hydrophilic, water swellable particles are cellulose and the cellulose is carboxymethylcellulose.

5. The skin plaster as claimed in claim 1, wherein the water-vapor-permeable back layer is formed from a material selected from the group which comprises polyethylene films, polypropylene films, polyvinyl chloride films, polyether amide films, polyamide films, polyester films, ethylene vinyl acetate films, woven fabrics, knitted fabrics, foams and polyurethane films.

6. The skin plaster as claimed in claim 1, wherein the water-vapor-permeable back layer is microporous or perforated.

7. The skin plaster as claimed in claim 1, wherein the water vapor permeability in a period of 24 hours is at least 80 g/m².

8. The skin plaster as claimed in claim 1, wherein the skin plaster further comprises an absorbent covering.

9. The skin plaster as claimed in claim 1, wherein the skin plaster additionally has a single-part or multi-part, detachable protective layer or protective film which completely or partly covers the adhesive layer on a surface facing the water-vapor-permeable back layer.

10. The skin plaster as claimed in claim 1, wherein the at least one antiviral active ingredient is present in an amount of 0.1 to 20% by weight of said adhesive layer.

11. The skin plaster as claimed in claim 1, wherein the adhesive layer has a thickness of between 25 μm to 200 μm.

\* \* \* \* \*